United States Patent [19]

Schroth et al.

[11] Patent Number: 5,202,353
[45] Date of Patent: Apr. 13, 1993

[54] IRON ENHANCEMENT OF COPPER BASED FUNGICIDAL AND BACTERICIDAL COMPOSITIONS

[75] Inventors: Milton N. Schroth, Orinda; Yung-Ann Lee, Albany; Mavis D. Chong, El Sobrante, all of Calif.

[73] Assignee: The Regents of the University of California, Oakland, Calif.

[21] Appl. No.: 644,997

[22] Filed: Jan. 22, 1991

[51] Int. Cl.$^5$ .............................................. A01N 55/02
[52] U.S. Cl. ....................................... 514/500; 514/502
[58] Field of Search ...................... 514/500, 499, 502; 71/67

[56] References Cited

U.S. PATENT DOCUMENTS

| | | | |
|---|---|---|---|
| 2,924,551 | 2/1960 | Harwood et al. | 167/22 |
| 4,101,669 | 7/1978 | Baude et al. | 424/286 |
| 4,193,993 | 3/1980 | Hilditch | 424/121 |
| 4,670,429 | 6/1987 | Dombay et al. | 514/187 |
| 4,745,129 | 5/1988 | Ikari et al. | 514/502 |

OTHER PUBLICATIONS

Clarke et al., Applied and Envir. Microbio., May 1987 pp. 917–922.
Lodeman, "The Spraying of Plants", the MacMillan Company, New York, N.Y. (1910).
Millardet, "The Discovery of the Bordeaux Mixture" (1885) translated by Schneiderman (1933).
Millardet, Notes Sur Les Vignes Americaines et Opuscules Divers Sur le Meme Sujet, pp. 56–60 (1881) (No translation).
Journal D'Agriculture Pratique, pp. 698–700, 728–729, and 765–766 (1887) (No translation).
Schroth et al. "Research Proposal: New Approaches to Controlling Walnut Blight;" 1984 pp. 1–4.
Lodeman "The Spraying of Plants" 1910 pp. 10–49.

*Primary Examiner*—Glennon H. Hollrah
*Assistant Examiner*—Brian M. Burn
*Attorney, Agent, or Firm*—Burns, Doane, Swecker & Mathis

[57] ABSTRACT

Disclosed herein are copper based fungicidal and bactericidal compositions having enhanced activity against fungi and bacteria, methods of using such compositions as well as methods for increasing the effectiveness of the copper based fungicidal and/or bactericidal compounds employed in such compositions.

8 Claims, 3 Drawing Sheets

IRON ENHANCEMENT OF COPPER BASED FUNGICIDAL AND BACTERICIDAL COMPOSITIONS

BACKGROUND OF THE INVENTION

1. Field of the Invention

The present invention is directed to copper based fungicidal and bactericidal compositions, methods of using such compositions as well as methods for increasing the effectiveness of copper based fungicidal and/or bactericidal compounds. In particular, the present invention is directed to the discovery that the activity of copper based fungicidal and bactericidal compositions is unexpectedly enhanced by the addition of an activity enhancing amount of an iron ($Fe^{+3}$) compound to the fungicidal and bactericidal composition.

2. State of the Art

The use of copper based fungicidal and bactericidal compositions for agricultural uses is well known in the art. Their use and basic mode of operation has not significantly changed since their inception in the 1800's. In general, such compositions are applied to infested site in an amount sufficient to be toxic to the bacterial and/or fungal infestation. There have been no particular improvements made in these compositions except for developing smaller particles, using coppers of different solubilities, or adding "stickers" and "spreaders" to the material, as is done with many other pesticides. The addition of some dithiocarbamates have been reported as slightly increasing the effectiveness of copper compounds.

All of these copper based fungicidal and bactericidal compositions rely upon the toxic action of the free copper $+2$ ion (as opposed to chelated copper) which must penetrate into the microorganism in order to exert their toxic effect.

Because of their widespread use, some microorganisms have developed a dose dependent tolerance to copper based fungicidal and/or bactericidal compositions. That is to say that such microorganisms are tolerant to copper based fungicidal and/or bactericidal compositions at doses heretofore generally employed but, at higher dosages, free copper still exerts its toxic effect. However, the use of such higher dosages is not preferred for both economical and practical reasons.

On the other hand, it would be particularly advantageous if means were found to increase the effectiveness of such copper based fungicidal and/or bactericidal compositions so that the increased dosages of the compositions would not be required to kill even such resistant microorganisms. It would be even more advantageous if such means employed non-hazardous materials.

SUMMARY OF THE INVENTION

The present invention is directed to the discovery that the addition of iron ($Fe^{+3}$) to a copper based bactericidal and/or fungicidal composition results in a significant enhancement in the effectiveness of such copper based bactericidal and/or fungicidal compositions. The enhancement in the effectiveness of such copper based compositions is so great that fungicidal and/or bactericidal toxicity can be achieved at concentrations of free copper which, in the absence of iron, show little or no toxic effect on fungi and/or bacteria.

Accordingly, in one of its composition aspects, the present invention is directed to a fungicidal composition which comprises:
(a) a biologically inert carrier;
(b) an effective amount of a copper based fungicidal compound so as to be toxic to fungi in the presence of an activity enhancing amount of iron ($Fe^{+3}$); and
(c) an activity enhancing amount of iron ($Fe^{+3}$).

In another of its composition aspects, the present invention is directed to a bactericidal composition which comprises:
(a) a biologically inert carrier;
(b) an effective amount of a copper based bactericidal compound so as to be toxic to bacteria in the presence of an activity enhancing amount of iron ($Fe^{+3}$); and
(c) an activity enhancing amount of iron ($Fe^{+3}$).

In one of its method aspects, the present invention is directed to a method for the control of fungi which method comprises applying to said fungi or their growth habitat a fungicidal composition which comprises:
(a) a biologically inert carrier;
(b) an effective amount of a copper based fungicidal compound so as to be toxic to fungi in the presence of an activity enhancing amount of iron ($Fe^{+3}$); and
(c) an activity enhancing amount of iron ($Fe^{+3}$).

In another of its method aspects, the present invention is directed to a method for the control of bacteria which method comprises applying to said bacteria or their growth habitat a bactericidal composition which comprises:
(a) a biologically inert carrier;
(b) an effective amount of a copper based bactericidal compound so as to be toxic to bacteria in the presence of an activity enhancing amount of iron ($Fe^{+3}$); and
(c) an activity enhancing amount of iron ($Fe^{+3}$).

In still another of its method aspects, the present invention is directed to a method for enhancing the effectiveness of a copper based bactericidal and/or fungicidal composition which method comprises the steps of:
selecting a copper based bactericidal and/or fungicidal composition; and
adding an activity enhancing amount of iron ($Fe^{+3}$) to said composition so as to enhance the toxicity of said composition to bacteria and/or to fungi.

The practice of the invention is very simple and involves only the addition of soluble iron compounds to copper based fungicidal and bactericidal compositions. The methods for applying such compositions will not be changed from those well known in the art, except that at the same concentration of free copper, the compositions of this invention will be more effective in controlling fungi and bacteria as compared to similar compositions not containing soluble iron compounds. As a corollary to this, the amount of free copper required in the compositions of this invention to effect toxicity to fungi and/or bacteria will be less than that previously used in similar compositions not containing soluble iron compounds. A particular advantage of the present invention resides in the fact that many $Fe+3$ salts are relatively non-hazardous and accordingly, their use in enhancing the efficacy of copper based fungicidal and bactericidal compositions is achieved without introducing potentially hazardous materials into the environment.

In this regard, the addition of such an activity enhancing amount of one or more iron compounds to the copper based fungicidal and/or bactericidal composition enhances the efficacy of these materials. Without being limited to any theories, it is believed that there are at least three different mechanisms which cause the increased efficacy:

1) at rates of at least about 10 ppm, preferably, from about 10 to about 300 ppm, and more preferably, from about 10 to about 100 ppm, the ferric ion, when incorporated with into the copper based fungicidal and/or bactericidal composition, interacts synergistically with the copper ion causing the bacterium and fungus to have enhanced susceptibility to the toxic action of the copper ion;

2) ferric ions on the plant leaf help to prevent chelation of copper by other substances. As noted above, chelation renders the copper ion non-toxic to fungal and bacterial microorganisms; and 3) the addition of ferric ions to suspensions or solutions containing copper based fungicidal and bactericidal compounds such as the fixed coppers results in a lowering of pH of the suspension or solution causing increased solubilization of copper ions. This occurs, in part, because the ferric ion has a greater affinity to anions such as $-OH$ than does the copper ion, thereby causing the release of free copper ions. On the leaf surface, such as on walnut leaves, the addition of iron to fixed coppers results in up to a 30 fold increase of the free copper ion. Also, lower pH, by itself, appears to have a toxic effect on bacterial microorganisms. However, lower pHs may not be preferred for fungal microorganisms.

Field experiments showed that the combination of iron with fixed coppers resulted in a statistically significant reduction of walnut blight bacteria (*Xanthomonas campestris* pv. juglandis) in walnut buds. The addition of iron to copper compounds used as wood preservatives also results in the increase of free copper ions, which inhibit wood rotting fungi.

Accordingly, this invention enhances the toxic action of the copper compounds by both increasing the susceptibility of the organism to the toxic action of the ion and by causing more free copper ions to be present at the target sites.

The invention will be further illustrated by the following examples, which are intended to be purely exemplary of the invention. In these examples, the following abbreviations have the following meanings:

CYE—casitone-yeast extract
gal.—gallon
lbs—pounds
mV—millivolts
nm—nanometers
ppm—parts per million
rpm—rotations per minute

EXAMPLES

Example 1

This example examines the effect on toxicity to the both a copper-sensitive bacterium (*Xanthomonas campestris* pv. juglandis strain NF) and a copper-resistant bacterium (*Xanthomonas campestris* pv. juglandis strain C 1) arising from combining different metal ions with free $Cu^{+2}$ ions. In particular, a known density of the bacteria were spread on different CYE-glycerol agar medium containing different kinds of metal ions. The metals employed were $Fe^{+3}$ (from $FeCl_3$ and reported as Fe); $Cu^{+2}$ (from $CuSO_4$ and reported as Cu); $Mn^{+2}$ (from $MnSO_4$ and reported as Mn); $Mg^{+2}$ (from $MgCl_2$ and reported as Mgc); $Mg^{+2}$ ($MgSO_4$ and reported as Mgs); $Ca^{+2}$ (from $CaCl_2$ and reported as Ca); $Na^+$ (from NaCl and reported as Na); and $K^+$ (from KCl and reported as K).

The recovery of cells or the number of colonies that grew were compared to the control (CYE-glycerol agar medium without metal amendments) which provides an estimate of the toxicity of the ions. The less cells that are recovered means that the kill of bacteria is better.

Figure 1A:
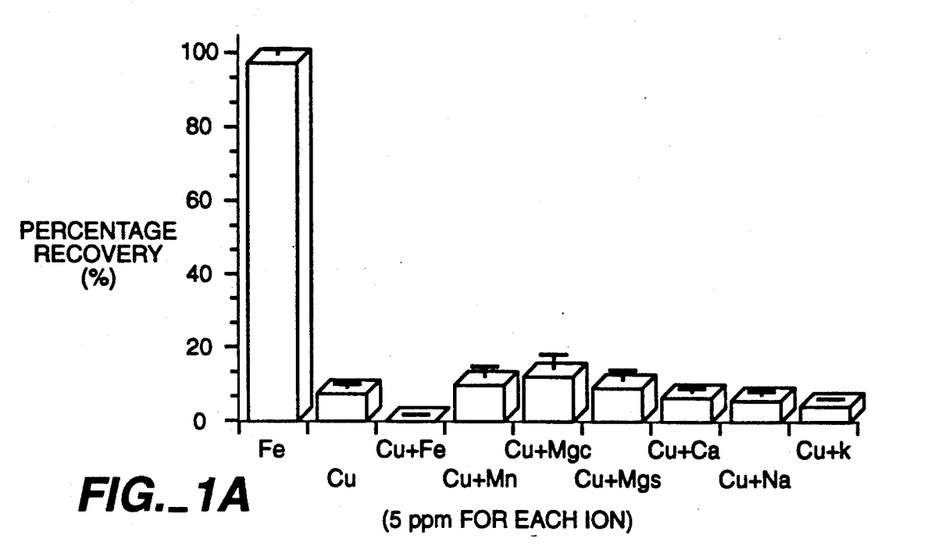
FIG. 1A illustrates the synergistic action of a copper based bactericidal compound and an iron compound in killing copper-sensitive strains of walnut blight bacteria, *Xanthomonas campestris* pv. juglandis.
Figure 1B:
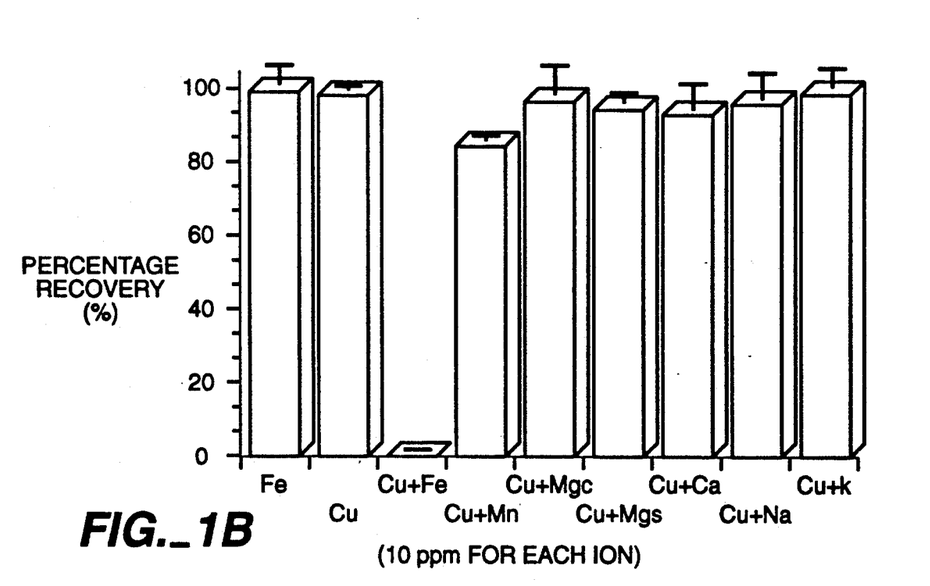
FIG. 1B illustrates the synergistic action of a copper based bactericidal compound and an iron compound in killing copper-resistant strains of walnut blight bacteria, *Xanthomonas campestris* pv. juglandis.

The results of these tests are shown in FIG. 1A (for the copper-sensitive bacterium) and in FIG. 1B (for the copper-resistant bacterium). In these figures, the results are given as a percentage recovery of the bacterium as compared to that recovered from the control. In particular, FIG. 1A illustrates that for the copper-sensitive bacterium, 5 ppm of an iron ($Fe^{+3}$) compound had little or no toxic effect whereas the addition of 5 ppm of copper resulted in a significant toxic effect regardless of whether the copper was used alone or in combination with other metal ions. In any event, the most toxic effect was seen for the copper/iron combination which resulted in substantially complete kill of all cells of the bacterium.

On the other hand, FIG. 1B illustrates that for the copper-resistant bacterium, the addition of 10 ppm of either an iron ($Fe^{+3}$) compound or a copper ($Cu^{+2}$) compound had little or no toxic effect on the bacterium. Likewise, FIG. 1B further illustrates that the addition of all combinations of 10 ppm of a copper ($Cu^{+2}$) compound with 10 ppm of other metal ions, except ferric ions, also had little or no toxic effect on the bacterium. However, the combination of 10 ppm of a copper ($Cu^{+2}$) compound with 10 ppm of an iron ($Fe^{+3}$) compound resulted in a substantially complete kill of all cells of the bacterium.

Accordingly, the results of these examples demonstrate that combinations of an iron ($Fe^{+3}$) compound and a free copper ($Cu^{+2}$) compound unexpectedly result in enhanced toxicity to bacteria and that these results are not shared by combinations of other metals with free copper.

Example 2

This example illustrates how varying concentrations of iron affect the synergistic action of iron and copper in killing copper sensitive or resistant bacteria. Specifically, copper resistant bacteria (*Xanthomonas campestris* pv. vesicatoria strain 81-23; *Pseudomonas syringae* pv. syringae strain A1513, and *Xanthomonas. campestris* pv. juglandis) were grown in the manner of Example 1 above at varying concentrations of copper and iron so as to determine concentrations of each required to inhibit the growth of these bacteria. The results of this example are reported in Tables 1-3 below. Table 1 describes the growth results for *Xanthomonas campestris* pv. vesicatoria copper-resistant strain 81-23 on the CYE-glycerol agar medium containing different concentrations of copper and iron.

TABLE 1

| Growth of X. c. pv. vesicatoria | | | | | |
|---|---|---|---|---|---|
| added conc. of $Fe^{3+}$ | added conc. of $Cu^{3*}$ (ppm) | | | | |
| (ppm) | 40 | 30 | 20 | 10 | 0 |
| 0 | − | + | + | + | + |
| 2.5 | − | ± | + | + | + |
| 5.0 | − | − | ± | + | + |
| 10.0 | − | − | − | + | + |

[1]The bacterium was streaked to the agar plates and grown at 28° C. for 2-3 days. + growth; ± poor growth; − no growth.

Table 2 describes the growth results for *pseudomonas syringae* pv. syringae copper-resistant strain A1513 on the CYE-glycerol agar medium containing different concentrations of copper and iron.

TABLE 2

| Growth of P. s. pv. syringae[2] | | | | | |
|---|---|---|---|---|---|
| added conc. of $Fe^{3+}$ | added conc. of $Cu^{2+}$ (ppm) | | | | |
| (ppm) | 40 | 30 | 20 | 10 | 0 |
| 0 | + | + | + | + | + |
| 2.5 | − | ± | + | + | + |
| 5.0 | − | − | ± | + | + |
| 10.0 | − | − | − | + | + |

[2]The bacterium was streaked to the agar plates and grown at 28° C. for 2-3 days. + growth; ± poor growth; − no growth.

Table 3 describes the growth results of *Xanthomonas campestris* pv. juglandis copper-resistant strain C1 on the CYE-glycerol agar medium containing different concentrations of copper and iron.

TABLE 3

| Growth of X. c. pv. juglandis[3] | | | | | |
|---|---|---|---|---|---|
| added conc. of $FE^{3+}$ | added conc. of $Cu^{2+}$ (ppm) | | | | |
| (ppm) | 40 | 30 | 20 | 10 | 0 |
| 0 | ± | + | + | + | + |
| 2.5 | − | ± | + | + | + |
| 5.0 | − | − | ± | + | + |
| 10.0 | − | − | − | + | + |

[3]The bacterium was streaked to the agar plates and grown at 28° C. for 2-3 days. + growth; ± poor growth; − no growth The above data demonstrates that with increased concentrations of iron, less copper is needed to inhibit the growth of *Xanthomonas campestris* pv. vesicatoria, *Pseudomonas syringae* pv. syringae, and *Xanthomonas campestris* pv. juglandis.

Example 3

This example demonstrates that the addition of $Fe^{3+}$ (up to 200 ppm) to an aqueous copper based bactericidal composition (Kocide 101—available from Griffin Ag Products, Valdosta, Ga.) does not impede the ability of the cupric electrode to measure free copper ion ($Cu^{2+}$) concentrations. Specifically, the aqueous copper based bactericidal compositions were amended with $FeCl_3$ (where necessary) and then were centrifuged at 14,000 rpm for 30 minutes and the dissolved copper concentrations of supernatants were measured with an inductively coupled plasma (ICP) 40 emission spectrometer (Perkin-Elmer Corporation). On the other hand, free copper concentrations of Kocide solutions amended with $FeCl_3$ (where necessary) were measured directly with a cupric specific electrode (Orion model 9429). The pH of the solution was measured with a pH meter. The results of this test are set forth in Table 4 below:

TABLE 4

| | Kocide | | |
|---|---|---|---|
| Added $Fe^{3+}$ (ppm) | Dissolved copper[4] (ppm) | Free copper[5] (ppm) | pH |
| 0.0 | 0.08 | 0.02 | 7.8 |
| 20.0 | 22.60 | 20.99 | 6.0 |
| 50.0 | 68.50 | 66.99 | 5.9 |
| 100.0 | 145.30 | 152.41 | 5.6 |
| 200.0 | 287.50 | 321.47 | 5.4 |

[4]Kocide solutions amended With $FeCl_3$ were centrifuged at 14,000 rpm for 30 min, and the dissolved copper concentrations of supernatants were measured with the inductively coupled plasma (ICP) 40 emission spectrometer (Perkin-Elmer corporation).

[5]Free copper concentrations of Kocide solutions amended with $FeCl_3$ were measured directly with a cupric specific electrode (Orion model 9429)

Example 5

Example 5 demonstrates that the addition of a soluble iron ($Fe^{3+}$) compound to the CYE glycerol broth medium decreased pH values and increased the availability of free copper ions. Specifically, the pH values and copper electrode potential (mV) were determined for CYE-glycerol broth containing different concentrations of added free copper ($Cu^{2+}$) and added iron ($Fe^{3+}$). The copper electrode potential (mV) was measured with a cupric specific electrode (Orion model 9429) and is proportional to logarithmic concentration of soluble free copper ion, i.e., 113 mV, 0.1 ppm; 146 mV, 1.0 ppm; 175 mV, 10.0 ppm. The results of this example are set forth in Table 5 below:

TABLE 5

| Iron (ppm) | Added Conc. of $Cu^{2+}$ (ppm)[6] | | | | | | | | | |
|---|---|---|---|---|---|---|---|---|---|---|
| | 5 | | 10 | | 20 | | 30 | | 40 | |
| | pH | mV | pH | mV | pH | mV | pH | mV | pH | mV |
| 0 | 6.78 | 12.4 | 6.51 | 52.2 | 5.78 | 104.4 | 5.42 | 133.3 | 5.12 | 150.4 |
| 1 | 6.73 | 16.3 | 6.39 | 56.8 | 5.80 | 106.8 | 5.38 | 134.6 | 5.08 | 151.2 |
| 5 | 6.46 | 28.6 | 6.10 | 76.3 | 5.50 | 120.7 | 5.21 | 140.8 | 5.00 | 155.1 |
| 10 | 5.88 | 61.5 | 5.65 | 101.2 | 5.19 | 133.4 | 4.98 | 147.8 | 4.82 | 159.9 |

[6]Each value given is a mean of six subsamples; the experiment was repeated once.

Example 6

As shown in Example 5 above, the addition of an iron ($Fe^{+3}$) compound to a laboratory growth medium containing a copper based bactericidal composition resulted in more free copper ($Cu^{+2}$) in the medium. This example demonstrates that the increased amount of free copper ($Cu^{+2}$) arising from the addition of an iron ($Fe^{+3}$) compound to the growth medium also arises when this combination is sprayed onto typical sites for application of such bacterial compositions, i.e., a walnut leaf surface.

In particular, concentrations of free copper ($Cu^{+2}$) were determined on walnut leaf surfaces sprayed with a Kocide 101 (a commercially available copper based bactericidal composition) solution at a concentration of 2 lb/100 gallons amended with different concentrations of the same iron ($Fe^{+3}$) compound. In each case, the amount of spray solution applied per unit area was kept constant and each experiment was repeat 3 times and each replication had three subsamples.

After spraying, the free copper concentration was determined by washing the leaf surface with water and determining the free copper concentration by measuring the copper electrode potential (mV) of the resulting aqueous solution with a cupric specific electrode (Orion model 9429).

Figure 2:
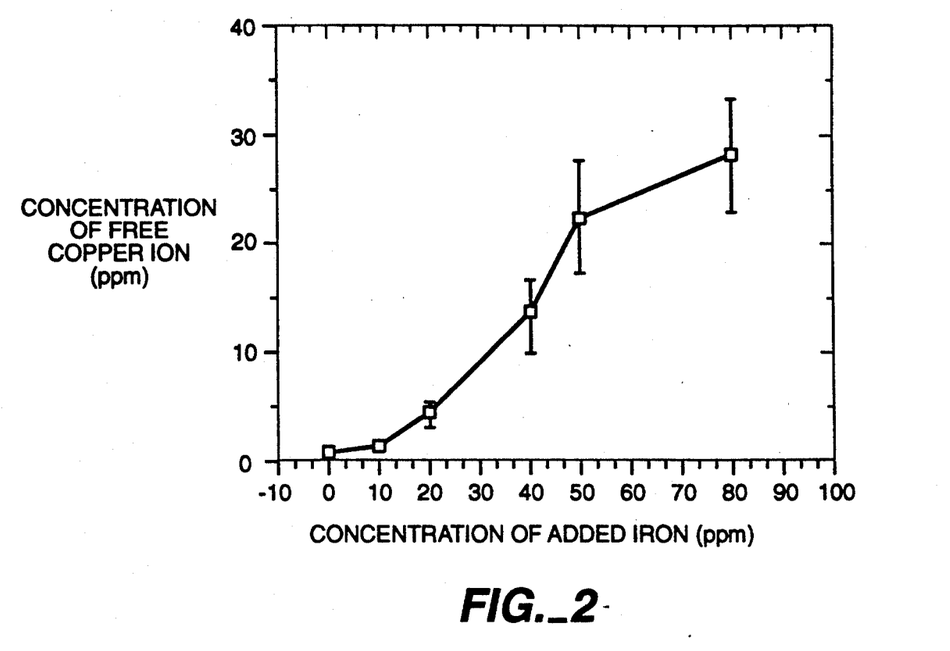
FIG. 2 illustrates that spraying walnut leaves with a solution of Kocide 101 (a commercially available copper based bactericidal composition) amended with iron significantly increased the availability of free copper ions on the leaf surfaces as compared to the nonamended Kocide spray.

The results of this example are set forth in FIG. 2 and each value is a mean of nine subsamples and is expressed as the mean ± the standard deviation (Std. Dev.). In particular, FIG. 2 illustrates that walnut leaves sprayed with a solution of Kocide 101 amended with an iron ($Fe^{+3}$) compound significantly increased the amount of free copper on the leaf surfaces as compared to the nonamended Kocide spray.

Example 7

The above examples have demonstrated that the addition of iron ($Fe^{+3}$) increases the amount of free copper ($Cu^{+2}$) in the medium because of the decreased pH values. This example demonstrates that the enhanced toxic effect resulting from the addition of an iron ($Fe^{+3}$) compound to the free copper ($Cu^{+2}$) does not arise solely from increased amounts of free copper ($Cu^{+2}$) in the medium.

Figure 3A:
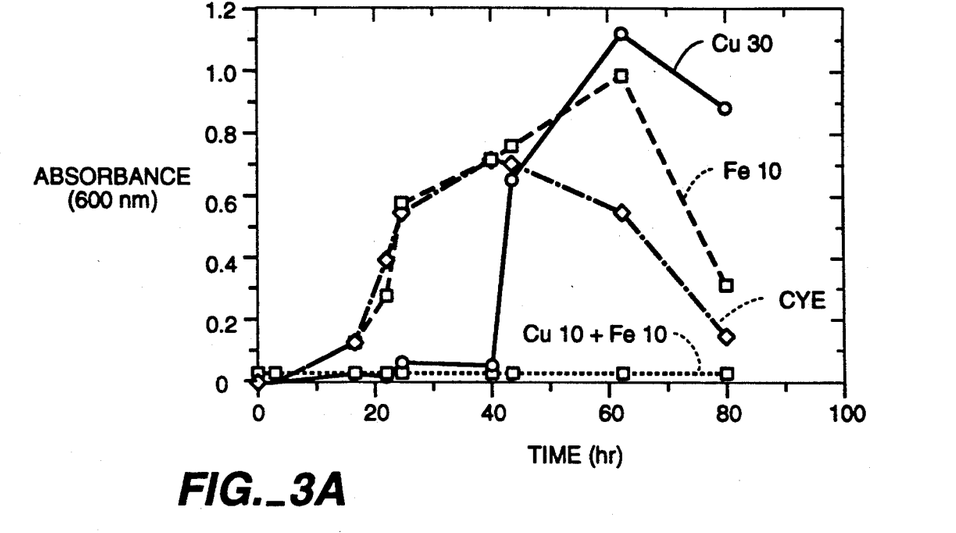
FIGS. 3A and FIG. 3B show that the addition of iron increased the amount of free copper ions in the medium because of the decreased pH values, but also affected the physiology of the bacteria making them more sensitive to the toxic action of the copper ions. Data also show that copper resistant strains of Xanthomonas campestris pv. juglandis and *Pseudomonas syringae* pv. syringae grow well after a period of lag phase in the medium with 30 ppm added copper even though the medium had a solution and that, in some cases, such higher concentrations of free copper can be phytotoxic to some plants. The specific concentration of free copper required for phytotoxicity will vary depending on the plant, ambient conditions and other factors. However, in general, copper based fungicidal and/or bactericidal compositions containing about 300 ppm or less of iron ($Fe^{+3}$) do not generate so much free copper so as to impart phytotoxicity to plants. Accordingly, in a preferred embodiment, the concentration of the iron ($Fe^{+3}$) compound employed in combination with the free copper composition is about 300 ppm or less. On the other hand, if phytotoxicity is not of any concern, then concentrations of iron ($Fe^{+3}$) of greater than 300 ppm can be used.
Figure 3B:
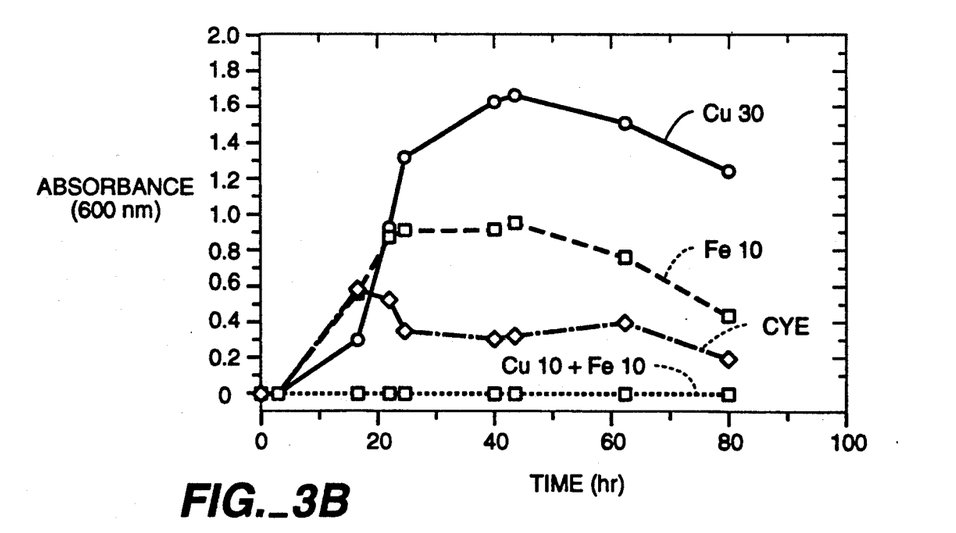

Specifically, this example analyzes the toxic effect of different concentrations of $Fe^{+3}$ metal ions with free $Cu^{+2}$ ions on the growth of copper-resistant bacteria (*Xanthomonas campestris* pv. juglandis strain 3E and *Pseudomonas syringae* pv. syringae copper-resistant strain A1513). This example was conducted by spreading a known concentration of these bacteria on different CYE-glycerol agar media containing different concentrations of $Fe^{+3}$ metal ions with free $Cu^{+2}$ ions. The concentration of metals employed were a control, i.e., 0 ppm $Fe^{+3}$ and 0 ppm $Cu^{+2}$ (reported in FIGS. 3A and 3B as CYE); an iron compound only, i.e., 10 ppm $Fe^{+3}$ and 0 ppm $Cu^{+2}$ (reported in FIGS. 3A and 3B as Fe 10); a copper compound only, i.e., 30 ppm of free $Cu^{+2}$ (reported in FIGS. 3A and 3B as Cu 30); and both an iron compound and a copper compound, i.e., 10 ppm of $Fe^{+3}$ and 10 ppm of $Cu^{+3}$ (reported as Cu10+Fe10 in FIGS. 3A and 3B).

The ability to inhibit growth of bacteria using these growth media was determined by measuring the absorbance of the growth media at 600 nm at various times. Specifically, the absorbance of the media correlates to growth occurring in the media with higher absorbance values indicating more growth. The results of this example are set forth in FIG. 3A, FIG. 3B and Table 5. Both of these figures establish that the combination of the free copper ($Cu^{+2}$) compound with an iron ($Fe^{+3}$) compound provides synergistic control over growth of the bacteria.

The data also show that both copper resistant bacterial strains grow well after a period of lag phase in the medium with 30 ppm added copper even though the medium had a low pH value and high free copper ion content (see Table 5). However, the bacteria did not grow in a medium with 10 ppm each of $Cu^{+2}$ and $Fe^{+3}$, which had a higher pH value and a lower content of free copper ($Cu^{+2}$). This indicates that the enhanced activity of free copper ($Cu^{+2}$) in the presence of an iron ($Fe^{+3}$) compound does not arise solely because this combination lowers the pH of the medium and thereby resulting in increased concentrations of free copper ($Cu^{+2}$). In fact, this data demonstrates that the iron ($Fe^{+3}$) compound increases the suspectibility of the bacteria to free copper.

Example 8

This example compares the effect on toxicity to both a copper-sensitive bacterium (*Xanthomonas campestris* pv. juglandis strain NF 1) and a copper-resistant bacterium (*Xanthomonas campestris* pv. juglandis strain C 1) arising from treating walnut leaves infested with one of these microorganisms with compositions containing free copper ($Cu^{+2}$) plus specified amounts of an iron ($Fe^{+3}$) compound or with a composition containing free copper ($Cu^{+2}$) in the absence of an iron ($Fe^{+3}$) compound.

In particular, a known density of the bacteria was spread on individual walnut leaf surfaces which were then treated with Kocide 101 (2 lbs/100 gal) amended with different concentrations the same iron ($Fe^{+3}$) compound. In each case, the amount of spray solution applied per unit area was kept constant and each experiment was repeat 3 times and each replication had three subsamples.

The recovery of cells or the number of colonies that grew after treatment was compared to the control (leaves containing the bacterium but which were not treated with either a free copper composition or a free copper composition containing an iron compound). The results provide an estimate of the toxicity of the different combinations. The less cells that are recovered means that the kill of bacteria is better.

Figure 4:
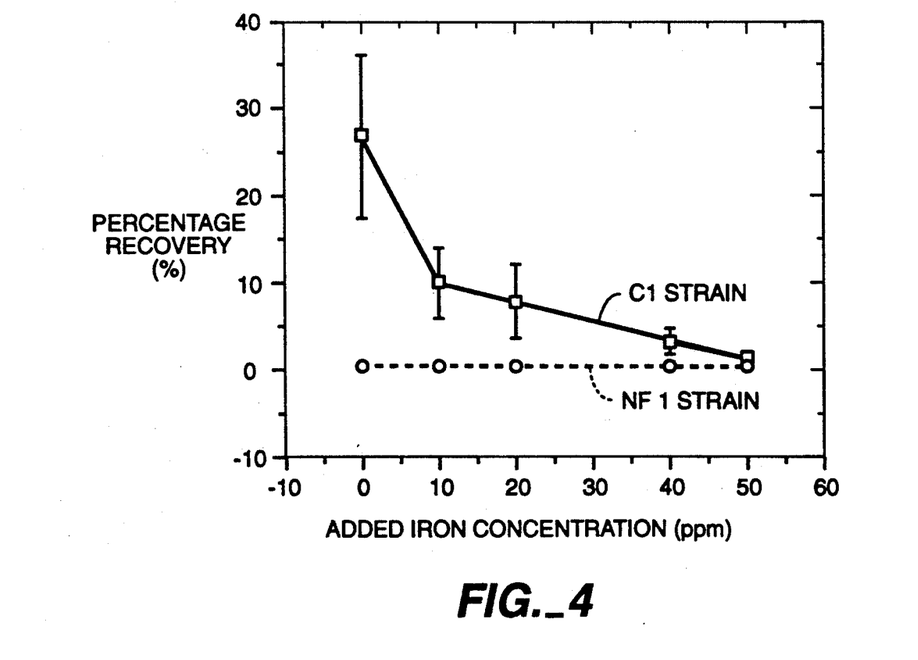

The results of this example are illustrated in FIG. 4 which provides the results as a mean of nine subsamples and the values reported in this figure are the mean of these subsamples and are expressed as the mean ± Std. Dev. In particular, FIG. 4 demonstrates that the copper sensitive strain was effectively killed by the addition of only free copper ($Cu^{+2}$) and that the addition of an iron ($Fe^{+3}$) compound has no additional effect because the amount of free copper is already sufficient to be toxic to this bacterium. On the other hand, this example further demonstrates that the copper-resistant bacterium was not completely killed by the amount of free copper employed but with increasing amounts of an iron ($Fe^{+3}$) compound, an enhancement in toxicity was seen.

Accordingly, the enhancement in toxicity achieved by the addition of an iron ($Fe^{+3}$) compound to a copper based bactericidal composition is seen not only in the CYE growth medium but also on a suitable sites for application of this composition.

Example 9

This example investigates the effectiveness of a composition of this invention against walnut blight. Walnut blight arises by colonization of newly developing buds early in spring by bacteria, i.e., *Xanthomonas campestris* pv. juglandis. The bacteria then overwinter in these sites until the buds develop into shoots the following year. These symptomless buds harbor populations of blight bacteria of between 10,000 and 100,000 per bud. In general, colonization of buds does not occur until the first rains and the bacteria are generally first found on the external surfaces and then later within the buds.

This example examines the toxic effect achieved by spraying walnut buds with a free copper based bactericidal composition (2 lbs./100 gal of Kocide 101); with the same composition amended to contain 50 ppm of an iron ($Fe^{+3}$) compound; with a composition containing 50 ppm of an iron ($Fe^{+3}$) compound and no free copper; and with a control composition, i.e., no free copper and no iron ($Fe^{+3}$) compound.

New buds are formed in April and infestations occur during rainfall. Buds are the principal source of inoculum. Accordingly, spraying was initiated on April 16 and sprayed 4 times at intervals of 7 to 10 days. First samples were collected on May 21 and second samples on June 3 after 3 inches of rain. The results of this example are set forth in Table 6 below:

TABLE 6

Percentage of walnut buds infested with
*Xanthomonas campestris* pv. juglandis on walnut
trees with different treatments.[7,8,9]

| Treatments | before rain | after rain |
|---|---|---|
| Kocide 101 | 10.7[ab] | 23.3[a] |
| Kocide 101 + 50 ppm $Fe^{3+}$ | 3.3[a] | 6.0[b] |
| 50 ppm $Fe^{3+}$ | 17.9[bc] | 68.7[c] |
| Control | 28.3[c] | 75.3[c] |

[7]Values are the mean number for each treatment replicated five times in completely randomized design at two different experimental sites. 175-200 buds for each treatment were assayed for the presence of X. c. pv juglandis.
[8]Means with a column followed by the same letter are not significantly different (P = 0.05), least significant different = 13.8 (before rain) and 16.1 (after rain).
[9]Kocide 101 were applied at the rate of 2 lb/100 gal. All treatments were applied to the Ashley variety.

The above results demonstrate that, after rainfall, the buds treated with the composition of this invention provided substantially better protection against walnut blight as compared to the buds treated with only Kocide 101 and that treatment with only iron ($Fe^{+3}$) was substantially equivalent to control. That is to say that treatment with an iron ($Fe^{+3}$) compound in the absence of a free copper compound provided little, if any, protection against the blight.

Example 10

This example ascertains to what extent siderophores are involved in the mechanism by which iron ($Fe^{+3}$) enhances the toxicity of a free copper based fungicidal and/or bactericidal composition. In particular, siderophores are iron ($Fe^{+3}$) chelating compounds generated by a microorganism in response to iron deprivation. Siderophores are released from the microorganism whereupon they can complex with solubilized $Fe^{+3}$ compounds. These siderophore complexes can then be scavenged from these siderophore complexes through the use of specific membrane transport systems.

As noted above, it is only free copper (uncomplexed $Cu^{+2}$) that imparts toxicity to the microorganism. Moreover, siderophores which complex iron ($Fe+3$) may also complex free copper thereby rendering it inactive. In such a situation, it is possible that the addition of iron ($Fe+3$) to the free copper based fungicidal and/or bactericidal composition enhances the activity of the free copper by providing an alternative or preferred site for siderophore complexation.

This example determines whether such a siderophore mechanism is involved in the activity enhancing effect of iron ($Fe^{+3}$). Specifically, this example employs a siderophore deficient variant of *Pseudomonas syringae* pv. syringae (S−) and a variant capable of siderophore production of *Pseudomonas syringae* pv. syringae (S+).

In each case, a known density of the bacteria was spread on different CYE-glycerol agar medium in a petri dish containing the same concentration of a free copper compound and an iron ($Fe^{+3}$) compound. If siderophore production was involved in the mechanism by which the iron ($Fe^{+3}$) compound enhanced the activity of the free copper compound, then it would be expected that inhibition of the S+ strain would be greater than that of the S− strain. However, after about 48-72 hours, the inhibition of both strains was not different. That is to say that the degree of inhibition of the S+ strain was equivalent to the degree of inhibition of the S− strain. These results demonstrate that siderophores are not involved in the mechanism by which the iron ($Fe^{+3}$) compound enhances the activity of the free copper based fungicidal and/or bactericidal composition.

In addition to enhancing toxic effect of a free copper based bactericidal composition, iron ($Fe^{+3}$) compounds also enhance the toxic effect of a free copper based fungicidal composition. Such fungi include, for instance, fungi response for bean powdery mildew (*Erysiphe polygoni*), tomato late blight (*Phytophthora infestans*), grape downy mildew (*mopara viticola*), rice blast (*piricularia oryzae*), and the like.

Lastly, in treating certain blights, it is contemplated that, in addition to treatment with a composition of this invention, treatment of the situs with a microorganism benign to the situs but which is antagonistic to the blight may enhance control of the blight. For example, in the case of walnut blight caused *Xanthomonas campestris* pv. juglandis, it has been found that some buds are heavily populated with a yeast strain which is naturally inhibitory to the blight and a number of buds contained only the yeast. Moreover, the yeast appears to be tolerant to copper. Accordingly, cotreatment of a walnut blight situs with both a composition of this invention as well as such a yeast strain which is benign to the situs but antagonistic to the blight may improve the effect of the treatment.

What is claimed is:

1. A bactericidal composition which comprises:
    (a) a biologically inert carrier;
    (b) a fixed copper based bactericidal composition which provides a concentration of free copper of from about 1 to about 30 ppm so as to be toxic to bacteria in the presence of an activity enhancing amount of iron ($Fe^{+3}$); and
    (c) an activity enhancing amount of $Fe^{+3}$ which amount is not more than about 300 ppm.

2. A bactericidal composition according to claim 1 wherein said iron ($Fe^{+3}$) concentration is from about 10 to about 300 ppm.

3. An aqueous bactericidal composition which comprises:
    (a) water;
    (b) an effective amount of a fixed copper based bactericidal compound so as to provide from about 1 to about 30 ppm of free copper in the aqueous solution; and
    (c) a sufficient amount of a water soluble $Fe^{+3}$ compound so as to enhance the activity of the copper based bactericide which amount is not more than about 300 ppm of $Fe^{+3}$.

4. An aqueous bactericidal composition according to claim 3 wherein the $Fe^{+3}$ concentration is from about 10 to 300 ppm.

5. A method for the control of bacteria which method comprises applying to said bacteria or their growth habitat a bactericidal composition according to claim 1.

6. The method according to claim 5 wherein said bacteria is *Xanthomonas campestris* pv. juglandis.

7. A method for enhancing the effectiveness of a copper based bactericidal composition which method comprises the steps of:
    providing a fixed copper based bactericidal composition; and
    adding an effective amount of iron ($Fe^{+3}$), which amount is not more than about 300 ppm, to said composition.

8. A method according to claim 7 wherein said iron ($Fe^{+3}$) concentration is from about 10 to about 300 ppm.

* * * * *

UNITED STATES PATENT AND TRADEMARK OFFICE
CERTIFICATE OF CORRECTION

PATENT NO. : 5,202,353
DATED : April 13, 1993
INVENTOR(S) : Schroth et al.

Page 1 of 3

It is certified that error appears in the above-indentified patent and that said Letters Patent is hereby corrected as shown below:

Column 2, lines 56 and 60, "juglandis" should appear in italics.

Column 3, lines 5-6, "syringae" should appear in italics.

Column 3, line 48, "$Cu^{+2}$) The" should appear as -- $Cu^{+2}$). The--.

Column 4, line 44, "in situ" should appear in italics.

Column 6, lines 4, 30, and 31, "juglandis" should appear in italics.

Column 7, lines 21-23 and 30, "vesicatoria", "syringae", "Xanthomonas. campestris", and "juglandis" should all appear in italics.

Column 7, line 35, Table 1, "X. c." and "vesicatoria" should appear in italics.

Column 7, line 35, Table 1, a superscript 1 should appear at the end of vesicatoria.

Column 7, line 38, Table 1, "$Cu^{3°}$" should appear as -- $Cu^{2+}$ --.

Column 7, line 48, "syringae" should appear in italics.

Column 7, line 53, Table 2, "P.s." and "syringae" should appear in italics.

Column 7, line 66, "juglandis" should appear in italics.

Column 8, line 2, Table 3, "X. c." and "juglandis" should appear in italics.

UNITED STATES PATENT AND TRADEMARK OFFICE
CERTIFICATE OF CORRECTION

PATENT NO. : 5,202,353
DATED : April 13, 1993
INVENTOR(S) : Schroth et al.

It is certified that error appears in the above-indentified patent and that said Letters Patent is hereby corrected as shown below:

Column 8, line 3, Table 3, "$FE^{3+}$" should appear as -- $Fe^{3+}$ --.

Column 8, line 4, Table 3, "$Cu^{2+(ppm)}$" should appear as -- $Cu^{2+}(ppm)$ --.

Column 8, lines 16-18, "vesicatoria", "syringae" and "juglandis" should appear in italics.

Column 8, line 48, Table 4, footnote 4, "With" should appear as -- with --.

Column 9, line 10, Table 5, footnote "b" should appear as -- 6 --.

Column 9, lines 59-60, "juglandis" and "syringae" should appear in italics.

Column 10, lines 47-48, "juglandis" should appear in italics.

Column 11, line 28, "juglandis" should appear in italics.

Column 11, lines 53 and 62, Table 6, "juglandis", "X. c.", and "juglandis" should appear in italics.

UNITED STATES PATENT AND TRADEMARK OFFICE
CERTIFICATE OF CORRECTION

PATENT NO. : 5,202,353
DATED : April 13, 1993
INVENTOR(S) : Schroth et al.

It is certified that error appears in the above-indentified patent and that said Letters Patent is hereby corrected as shown below:

Column 12, lines 34-35, "syringae" should appear in italics.

Column 12, line 67, "juglandis" should appear in italics.

Column 14, line 14, "juglandis" should appear in italics.

Signed and Sealed this

Nineteenth Day of April, 1994

Attest:

BRUCE LEHMAN

*Attesting Officer*     *Commissioner of Patents and Trademarks*